United States Patent [19]

Gruffaz et al.

[11] 4,275,228

[45] Jun. 23, 1981

[54] CATALYTIC PREPARATION OF ETHYL ACETATE

[75] Inventors: Max Gruffaz, La Mulatiere; Odile Micaelli, Lyons, both of France

[73] Assignee: Rhone-Poulenc Industries, Paris, France

[21] Appl. No.: 39,565

[22] Filed: May 16, 1979

[30] Foreign Application Priority Data

May 17, 1978 [FR] France ................................ 78 15355

[51] Int. Cl.³ ............................................. C07C 67/05
[52] U.S. Cl. ................................................... 560/247
[58] Field of Search ........................................ 560/247

[56] References Cited

U.S. PATENT DOCUMENTS

| | | | |
|---|---|---|---|
| 2,678,332 | 5/1954 | Cottle | 560/247 |
| 3,037,052 | 5/1962 | Bortnick | 560/247 |
| 3,041,317 | 6/1962 | Gibbs | 260/543 F |
| 3,282,875 | 11/1966 | Connolly | 260/543 F |
| 3,362,987 | 1/1968 | Kronig | 560/247 |
| 3,624,053 | 11/1971 | Gibbs | 260/543 F |
| 3,678,099 | 7/1972 | Kemp | 560/247 |
| 3,882,093 | 5/1975 | Cavanaugh | 568/615 |
| 3,922,294 | 11/1975 | Leupold | 560/247 |
| 4,128,727 | 12/1978 | Leupold | 560/247 |

FOREIGN PATENT DOCUMENTS

| | | | |
|---|---|---|---|
| 2306586 | 8/1974 | Fed. Rep. of Germany | 560/247 |
| 49-100016 | 9/1974 | Japan | 560/247 |
| 7401563 | 8/1974 | Netherlands | 560/247 |

*Primary Examiner*—Natalie Trousof
*Assistant Examiner*—Michael Shippen
*Attorney, Agent, or Firm*—Burns, Doane, Swecker & Mathis

[57] ABSTRACT

In a process for the preparation of ethyl acetate by vapor phase reaction of ethylene with acetic acid, the improvement which comprises conducting said reaction in the presence of a catalytic amount of a solid, ion-exchange fluoropolymer comprising sulfonic acid moieties.

23 Claims, No Drawings

CATALYTIC PREPARATION OF ETHYL ACETATE

BACKGROUND OF THE INVENTION

1. Field of the Invention

The present invention relates to a novel process for the preparation of ethyl acetate from acetic acid and ethylene. The invention more particularly relates to the preparation of ethyl acetate by reacting acetic acid with ethylene in the vapor phase in the presence of a special type of ion exchange resin.

2. Description of the Prior Art

It is well known to the art to react acetic acid with ethylene in the presence of acid catalysts to obtain ethyl acetate. A certain number of catalysts and operating conditions have been proposed in the literature. Certain authors have tested various catalysts for carrying out the present reaction in the vapor phase, for example, Y. Murakami, T. Mattori and H. Uchida, *Kogyo Kagaku Zasshi*, Vol. 72, pages 1,945–1,948 (1968). In particular, Murakami et al compared the catalytic activity of mixtures of silicotungstic acid and silica gel, and of phosphoric acid and kieselguhr, with that of certain ion exchange resins such as AMBERLITE IR 120 B and AMBERLYST 15. The first is of the gelantinous type, while the second is of the macroporous type, and both are marketed by Rohm and Haas. Murakami et al concluded that both phosphoric acid on kieselguhr and AMBERLITE IR 120 B have virtually no catalytic activity in the present reaction. Furthermore, they demonstrated that, although the catalysts based on silicotungstic acid have an appreciable initial activity at relatively high temperatures, such catalysts are deactivated after only a few hours of operation. The efficiency of these catalysts in the present reaction is virtually zero at temperatures below 150° C., while at high temperatures, they cause the formation of acetone. Murakami et al showed that, although AMBERLYST 15 is the most efficient catalyst in the present reaction, it, too, becomes deactivated after only a few hours at the temperature required by the reaction.

Therefore, the catalysts of the first type are unsuitable for carrying out the present reaction in the gas phase because of their low activity, and use of the second type of catalysts, the resins suggested by the earlier prior art, has failed because of their instability and rapid deactivation at the temperatures required for the present reaction to proceed satisfactorily. In conclusion, the proposals of the prior art for preparing ethyl acetate by reacting ethylene with acetic acid in the vapor phase have not proved satisfactory on an industrial scale.

It is well known to the art that ethyl acetate is one of the most commonly used esters in industry because of its exceptional solvent properties. Therefore, it would be highly desirable to have available catalysts for the preparation of this ester by the present process which are both more efficient and more stable than the prior art catalysts. The potential value of having available such catalysts has already been widely recognized.

SUMMARY OF THE INVENTION

It is therefore an object of the present invention to make available catalysts for the process of preparing ethyl acetate by reacting ethylene with acetic acid in the vapor phase, which are both more stable and more efficient than the catalysts of the prior art and which are satisfactory for use on an industrial scale.

The present invention relates to a process for the preparation of ethyl acetate by reacting ethylene with acetic acid in the vapor phase in the presence of a solid, ion-exchange fluoropolymer which comprises pendant sulfonic acid groups. Preferably, the fluoropolymer comprises units selected from the group comprising a unit of structural formula:

    (I)

a unit of structural formula:

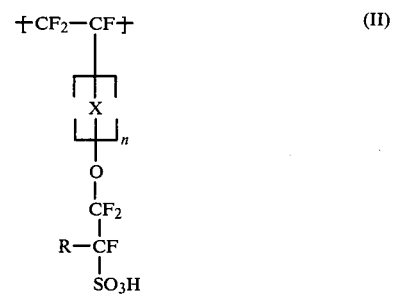    (II)

and a unit of structural formula:

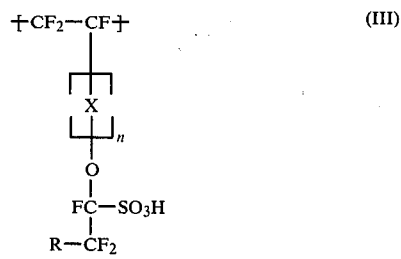    (III)

wherein n is an integer from 1 to 5, R is a fluorine atom or a monovalent perfluoroalkyl radical preferably having from 1 to 10 carbon atoms, and X is a radical selected from the group comprising a radical of structural formula:

    (i)

a radical of structural formula:

    (ii)

and, a radical of structural formula:

    (iii)

wherein m is an integer from 2 to 10, and Y is a fluorine atom or a trifluoromethyl group. The process of the present invention is surprisingly advantageous when compared with the previously proposed processes because the catalyst of the present invention is very efficient and its activity is virtually constant over a long period of time. In addition, virtually no by-products are formed.

DESCRIPTION OF THE PREFERRED EMBODIMENTS

Catalysts of the present invention comprise fluoropolymers having pendant sulfonic acid groups in an amount of from about 0.01 to 6 milliequivalents per gram of catalyst. These polymers preferably have from about 0.05 to 2 milliequivalents of pendant sulfonic acid groups per gram of catalyst.

The catalysts of the present invention which comprise units of structural formula (I), as defined above, are polymers of perfluoroalkenylsulfonic acids, or copolymers comprising these acids and fluoroethylenes, such as tetrafluoroethylene. These polymers can be prepared by the methods described in U.S. Pat. Nos. 3,041,317 and 3,624,053, which are hereby incorporated by reference.

The catalysts of the present invention which comprise units of structural formula (II) or structural formula (III), as defined above, can be prepared by one of several known methods. These methods are disclosed in U.S. Pat. Nos. 3,282,875 and 3,882,093, which are hereby incorporated by reference.

The preferred fluoropolymers comprise units of structural formula (II) or structural formula (III) wherein n is from 1 to 3, Y is a trifluoromethyl radical, R is a fluorine atom, and m is equal to 2.

A particularly advantageous class of polymers of this kind comprises the copolymers which are produced by the polymerization of perfluoroethylene with a perfluorovinyl ether having sulfonic acid groups, and which correspond to the following structural formula:

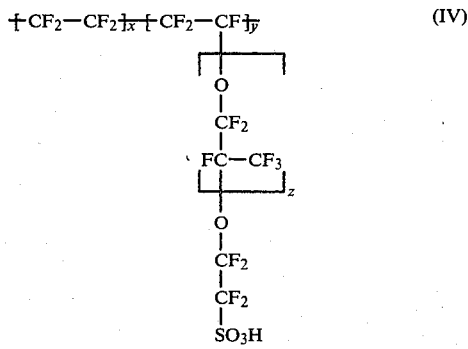

wherein z is an integer from 1 to 3, and the ratio of x to y is from 2 to 50, and preferably, from 5 to 13. Polymers of this class are resins marketed under the trademark NAFION. In addition to their commercial availability, these resins are advantageous because they offer a high concentration of accessible acid sites in the solid phase.

In the following text, these fluorine-containing polymers having sulfonic groups will be referred to as resins or catalysts, regardless of whether their structure is of structural formula I, II, III or IV.

The process of the present invention is carried out by introducing ethylene and acetic acid in the gaseous state into a reaction zone wherein a solid layer of the catalyst is present. The reaction time is dependent on the reaction conditions and can vary from less than 30 to more than 70 hours. The reaction is normally carried out at atmospheric pressure although high pressure can be used without difficulty.

The reaction temperature is usually carried out in the temperature range of from 100° to 200° C., however, it can also be carried out using slightly lower or higher temperatures. The reaction is preferably carried out in the temperature range of from 125° to 170° C. The molar ratio of ethylene to acetic acid is usually from 1 to 30, and preferably from 5 to 15. Preferably, the reaction medium is essentially anhydrous.

The process of the present invention is normally carried out continuously. For example, the reactants can be brought into contact with the catalyst in a vertical, tubular reactor which contains, in addition to a solid layer of catalyst, means for supporting the catalyst and means for preventing the solid catalyst from being carried away. For example, the catalyst layer can be supported on a metal grid, or between an upper layer and a lower layer of glass beads, ceramic beads, or glass wool. A preferred method of carrying out the process of the present invention comprises mixing the solid catalyst with an inert material such as quartz or silica.

In order to further describe the present invention, the following examples are provided; it being understood that these examples are merely illustrative and in nowise limitative.

EXAMPLES 1 TO 5

Preparation of the Catalyst

The catalyst used in the following examples was prepared from NAFION 501 powder, which is a commercial fluorine-containing polymer in the form of the potassium salt. The NAFION 501 powder was treated with a 5% hydrochloric acid solution, thereby converting the polymer from its potassium salt form into its acid form, rinsed with distilled water until the washings were neutral, and then dried at 100° C., in vacuo.

Process of the Reaction

50 $cm^3$ of the catalyst prepared above, which in some of the examples was mixed with an inert material, were introduced into a vertical, tubular glass reactor. The reactor has a length of 67 cm and a capacity of 90 $cm^3$ and was provided with a double envelope. Glass beads were then introduced into the upper part of the reactor. Subsequently, the reactor was heated by a fluid circulating in the double envelope and was fed with a descending stream of ethylene and acetic acid. The effluent was analyzed continuously by gas chromatography.

The inert material which was used in some of the examples was silica having a specific surface area of 400 $m^2/g$, a mean pore diameter of 80 Å, and a porous volume of 1 $cm^3/g$. A material of this kind is commercially available under the name SPHEROSIL XOA 400.

Table I summarizes the particular operating conditions and also the results obtained in Examples 1 to 5. In Table I, T° C. denotes the temperature in degrees centigrade; t denotes the reaction time expressed in hours; DC % denotes the initial degree of conversion of the acetic acid; and Y denotes the number of moles of ethyl acetate formed per kilogram of catalyst and per hour, corresponding to the initial degree of conversion.

TABLE I

| Example No. | Weight of Catalyst in g | Weight of Silica in g | C₂H₂ liters /hour | CH₃COOH g/ hour | T °C. | t | DC % | Y |
|---|---|---|---|---|---|---|---|---|
| 1 | 44.7 | 0 | 5.6 | 1.3 | 126 | 55 | 30.0 | 0.141 |
| 2 | 30.0 | 15.0 | 9.0 | 1.9 | 135 | 100 | 59.0 | 0.621 |
| 3 | 20.0 | 15.0 | " | 1.8 | " | 42 | 46.0 | 0.69 |
| 4 | " | " | " | " | 150 | 30 | 60.0 | 0.90 |
| 5 | 15.0 | 15.7 | " | 2.0 | " | 24 | 58.0 | 1.276 |

EXAMPLE 6

Under the conditions of Example 2 above, the degree of conversion of the acetic acid and the yield of ethyl acetate were determined after a reaction time of 100 hours. The degree of conversion was 48% and the yield of ethyl acetate in moles of ethyl acetate per kilogram of catalyst and per hour was 0.505. This demonstrates the lifetime of the catalyst because the activity of the catalyst was virtually undiminished after 100 hours of operation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the preparation of ethyl acetate by vapor phase reaction of ethylene with acetic acid, the improvement which comprises conducting said reaction in the presense of a catalytic amount of a solid, ion-exchange fluoropolymer comprising pendant sulfonic acid moieties, said fluoropolymer comprising recurring structural units selected from the group comprising a unit of structural formula (I):

$$+CF_2-CF+$$
$$|$$
$$SO_3H$$

a unit of structural formula (II):

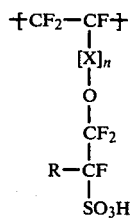

and a unit of structural formula (III):

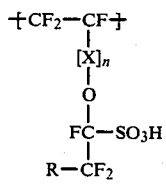

wherein, n is an integer from 1 to 5, R is a fluorine atom or a monovalent perfluoroalkyl radical comprising from 1 to 10 carbon atoms, and X is radical selected from the group comprising a radical of structural formula (i):

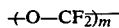

a radical of structural formula (ii):

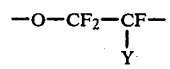

and, a radical of structural formula (iii):

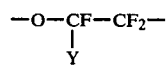

wherein, m is an integer from 2 to 10, and Y is a fluorine atom or a trifluoromethyl group.

2. The process as defined by claim 1, said fluoropolymer comprising a polymer of perfluoroalkenylsulfonic acid.

3. The process as defined by claim 1, said fluoropolymer comprising a copolymer of perfluoroalkenylsulfonic acid and fluoroethylene.

4. The process as defined by claim 3, said fluoroethylene comprising tetrafluoroethylene.

5. The process as defined by claim 1, said fluoropolymer comprising recurring structural units selected from the group comprising a unit of structural formula (II) and a unit of structural formula (III), wherein n is an integer from 1 to 3, R is a fluorine atom, m is equal to 2, and Y is a trifluoromethyl radical.

6. The process as defined by claim 1, said fluoropolymer comprising a copolymer prepared by the process comprising polymerizing perfluoroethylene with a perfluorovinyl ether, said ether comprising sulfonic acid groups.

7. The process as defined by claim 1, said fluoropolymer comprising a copolymer of structural formula (IV)

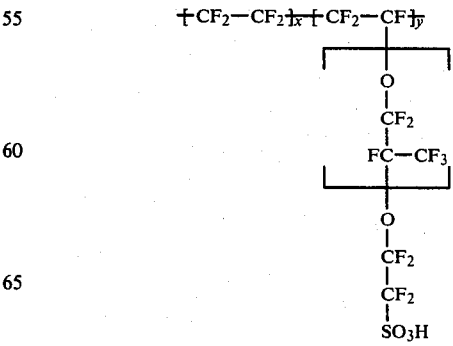

wherein, z is an integer from 1 to 3, and the ratio of x to y is from 2 to 50.

8. The process as defined by claim 7, said ratio of x to y being from 5 to 13.

9. The process as defined by claim 1, said fluoropolymer comprising recurring units of structural formula (I).

10. The process as defined by claim 1, said fluoropolymer comprising recurring units of structural formula (II).

11. The process as defined by claim 1, said fluoropolymer comprising recurring units of structural formula (III).

12. The process as defined by claim 10 or 11, wherein X is a radical of structural formula (i).

13. The process as defined by claim 10 or 11, wherein X is a radical of structural formula (ii).

14. The process as defined by claim 10 or 11, wherein X is a radical of structural formula (iii).

15. The process as defined by claim 1 or 7, said fluoropolymer comprising said sulfonic acid moieties in an amount from 0.01 to 6 milliequivalents per gram of said fluoropolymer.

16. The process as defined by claim 1 or 7, said fluoropolymer comprising from about 0.05 to 2 milliequivalents per gram of said sulfonic acid moieties.

17. The process as defined by claim 1 or 7, said reaction being carried out at a temperature of from about 100° to 200° C.

18. The process as defined by claim 17, said temperature being from about 125° to 170° C.

19. The process as defined by claim 1 or 7, wherein the molar ratio of said ethylene to said acetic acid is from 1 to 30.

20. The process as defined by claim 19, said molar ratio being from 5 to 15.

21. The process as defined by claim 1 or 7, said reaction being carried out under essentially anhydrous conditions.

22. The process as defined by claim 1 or 7, said fluoropolymer being mixed with a solid inert material.

23. The process as defined by claim 22, said inert material being selected from the group comprising quartz and silica.

* * * * *